US009730580B2

(12) United States Patent
Verdooner (10) Patent No.: US 9,730,580 B2
(45) Date of Patent: Aug. 15, 2017

(54) APPARATUS AND METHOD FOR DETECTING AMYLOID IN A RETINA IN A DIAGNOSIS, ADVANCEMENT, AND PROGNOSING OF ALZHEIMER'S DISEASE, TRAUMATIC BRAIN INJURY, MACULAR DEGENERATION AND A PLURALITY OF NEURODEGENERATIVE DISSORDERS, AND OCULAR DISEASES

(71) Applicant: NeuroVision Imaging, LLC, Sacramento, CA (US)

(72) Inventor: Steven Roger Verdooner, Granite Bay, CA (US)

(73) Assignee: NeuroVision Imaging LLC, Sacramento, CA (US)

( * ) Notice: Subject to any disclaimer, the term of this patent is extended or adjusted under 35 U.S.C. 154(b) by 742 days.

(21) Appl. No.: 14/191,398

(22) Filed: Feb. 26, 2014

(65) Prior Publication Data
US 2014/0180081 A1 Jun. 26, 2014

Related U.S. Application Data

(62) Division of application No. 13/280,161, filed on Oct. 24, 2011, now abandoned.
(Continued)

(51) Int. Cl.
*A61B 3/14* (2006.01)
*A61B 3/10* (2006.01)
*A61B 3/12* (2006.01)

(52) U.S. Cl.
CPC ............... *A61B 3/102* (2013.01); *A61B 3/12* (2013.01); *A61B 3/1208* (2013.01); *A61B 3/14* (2013.01)

(58) Field of Classification Search
CPC ......... A61B 3/0083; A61B 3/102; A61B 3/12; A61B 3/1241; A61B 5/1455; A61B 5/14555; A61B 5/14556; A61B 5/14507
(Continued)

(56) References Cited

U.S. PATENT DOCUMENTS 7,854,510 B2   12/2010  Verdooner
8,025,406 B2    9/2011  Zhang
(Continued)

FOREIGN PATENT DOCUMENTS

WO        2010033861 A1    3/2010

*Primary Examiner* — Huy K Mai
(74) *Attorney, Agent, or Firm* — Lucas & Mercanti, LLP; Peter J. Phillips (57) ABSTRACT

The present invention is an apparatus and method to produce an image of an eye of a patient that includes an optical head that includes imaging optics, illumination source optics and a camera housing with a perimeter that houses the video camera optics and the illumination source optics, a slit lamp chinrest and joystick assembly that includes an adjustable head support, a movable base, a joystick that adjusts a position of the camera housing relative to the head support and the housing support that mounts the video camera, a rubber eyecup that provides an interface between the camera housing and the patient's eye that protrudes outward from the perimeter and a computer system that analyzes images and data for the presence of amyloid in a retina, and other deposits and provides a diagnosis of macular degeneration, Alzheimer's disease, traumatic brain injury, multiple concussive injury, neurodegenerative and other ocular disorders.

15 Claims, 10 Drawing Sheets

Related U.S. Application Data (60) Provisional application No. 61/406,551, filed on Oct. 25, 2010.

(58) Field of Classification Search
USPC ......... 351/205, 206, 219; 600/309, 310, 476
See application file for complete search history.

(56) References Cited

U.S. PATENT DOCUMENTS

| | | |
|---|---|---|
| 2003/0184712 A1 | 10/2003 | Takeda |
| 2004/0019283 A1* | 1/2004 | Lambert ............ A61B 5/14532 600/476 |
| 2005/0094102 A1 | 5/2005 | Cornsweet |
| 2005/0134796 A1 | 6/2005 | Zelvin |
| 2005/0214222 A1 | 9/2005 | McKinnon |
| 2006/0215113 A1 | 9/2006 | Chernyak |
| 2007/0270350 A1 | 11/2007 | Singh |
| 2008/0188737 A1 | 8/2008 | Assmann |
| 2009/0096988 A1 | 4/2009 | Fink |
| 2010/0097573 A1 | 4/2010 | Verdooner |
| 2010/0259725 A1 | 10/2010 | Siminou |
| 2011/0051084 A1 | 3/2011 | Dobashi |
| 2011/0234977 A1 | 9/2011 | Verdooner |
| 2011/0286932 A1 | 11/2011 | Koronyo |
| 2012/0101371 A1 | 4/2012 | Verdooner |

* cited by examiner

APPARATUS AND METHOD FOR DETECTING AMYLOID IN A RETINA IN A DIAGNOSIS, ADVANCEMENT, AND PROGNOSING OF ALZHEIMER'S DISEASE, TRAUMATIC BRAIN INJURY, MACULAR DEGENERATION AND A PLURALITY OF NEURODEGENERATIVE DISSORDERS, AND OCULAR DISEASES

The present application is a divisional application of U.S. Non-Provisional application Ser. No. 13/280,161 filed on Oct. 24, 2011. The present application claims priority to U.S. Provisional Application 61/406,551 filed on Oct. 25, 2010, the entire of both disclosures are incorporated by reference herein.

TECHNICAL FIELD & BACKGROUND

Imaging of amyloid-beta plaques (including amyloid, amyloid-beta peptides) and other pathology and anatomical features in the retina or brain is often unobtainable without the use of specialized contrast agents, or autofluorescence techniques. While drusen and amyloid containing plaques may be visible in the retina with a variety of imaging techniques, specifically amyloid-beta plaques (including amyloid in other forms such as amyloid peptides) located in drusen, or other amyloid containing plaques (or in the retina or fundus at large) are not visible and verifiable as containing amyloid with any retinal imaging modalities with the sole exception of curcumin fluorescence/reflectance imaging that has been performed in vivo in animals only.

SUMMARY OF THE INVENTION

The apparatus and method can be used for the detection of amyloid in the retina and brain. This can be achieved solely with OCT by identification of a spectral signature of an amyloid in an OCT data set and or the anatomic location of plaques. The detection can also be achieved by varying the wavelength of the OCT device and analyzing the generated signal to derive an amyloid signal. This can also be achieved by a combination of OCT with multispectral imaging or the use of multispectral imaging alone or the use of autofluorescence or a contrast agent together with OCT. In each of the modalities the spectral signature can be obtained by spectral analysis and image processing. The image processing can identify the spectral wavelength and the spectral signature identified with amyloid in the retina and the brain using image processing techniques.

The apparatus and method utilizes a plurality of traditional optical coherence tomography (OCT) and current fundus imaging techniques for the visualization of amyloid in the retina or the brain through a combination of optical technology in combination with spectral analysis and image processing. By operating a plurality of OCT and multispectral imaging devices at a plurality of specific wavelengths a spectral signature of amyloid-beta plaques are allowed to be obtained from a data set utilizing image processing.

The apparatus and method utilizes a plurality of different operating modes and configurations such as a hand-held instrument or a mounted slit lamp, an integrated slit lamp, an integrated fundus camera, a scanning laser ophthalmoscope, or an optical head (such as a fundus camera) attached to a separate chinrest-joystick assembly.

The apparatus and method utilizes OCT and/or multispectral imaging in combination with standard or proprietary spectral wavelength selection, spectral analysis, and image processing to identify amyloid in the retina (or brain) rendering it visible to a clinician.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

As used herein, the terms "A beta peptides" and "A(beta) peptides" are interchangeable.

Figure 1A:
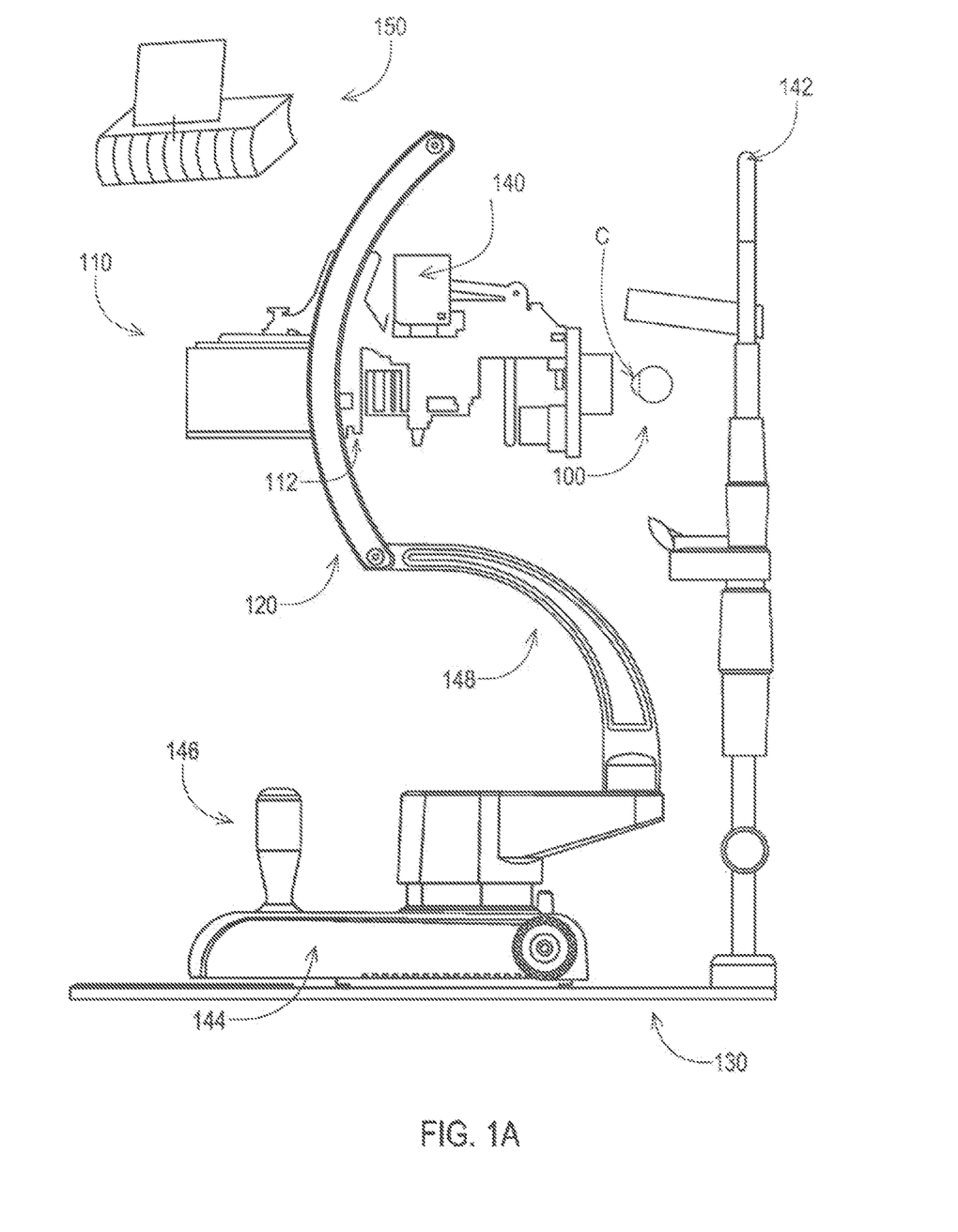
FIG. 1A illustrates a side perspective view of an apparatus for imaging an eye, in accordance with one embodiment of the present invention.

FIG. 1A illustrates an exploded perspective view of an apparatus 100 for producing an image of an eye, in accordance with one embodiment of the present invention. The image is an image of an amyloid-beta plaque, an amyloid or an amyloid-beta peptide or other pathology or anatomical features in the eye or brain of a user. The apparatus 100 detects the amyloid-beta plaque, the amyloid or the amyloid-beta peptide by a spectral signature. The apparatus 100 performs a maximum and minimum intensity projection (MIP/MinIP).

The apparatus for producing an image of an eye 100 includes a video camera 110, video camera optics 112, a camera housing 120 mounted on a slit lamp chinrest and joystick assembly 130 and illumination source optics 140. The video camera 110 is a digital camera but can be any type of suitable camera for use with the apparatus for producing an image of an eye 100. The slit lamp chinrest and joystick assembly 130 includes a head support 142, a movable base 144, a joystick 146, and a housing support 148. The head support 142 holds the patient's chin and forehead in a known, fixed position. The head support 142 is provided with a plurality of elevation adjustments to provide a comfortable resting place for the patient's head. The position of the camera housing 120 relative to the head support 142 can be adjusted in both relative gross and fine increments using the joystick 146. The apparatus for producing an image of an eye 100 is used in combination with a computer system 150, which is described in greater detail in FIG. 1D. The computer system 150 can be any suitable computer system 150 that can be used in combination with the apparatus for imaging an eye 100.

The apparatus 100 may be an optical coherence tomography device, as described below in conjunction with FIGS. 5, 6 and 7.

The personal computer 150 forms the center of the apparatus for imaging an eye 100, processing data and controlling the operation of other components of the apparatus for imaging an eye 100. Connected to the personal computer 150 is a video camera 110. An observation video monitor which can be the screen of the personal computer, a slit lamp chinrest and joystick assembly 130, illumination source optics 140, and video camera optics 112 are associated with the camera housing 120.

The personal computer 150 is a relatively compact computer, embedded computer, or tablet computer of relatively high processing power using a standardized operating system and having standardized card slots for interfacing peripheral equipment such as memory cards, video board, printer and a monitor. The personal computer 150 will run customized software as will be described in detail later. The monitor or screen of the personal computer will have very-high-resolution color graphics capability appropriate for displaying images under analysis.

The digitizing board accepts a digital file or video input from video camera 110 and functions as a "frame grabber," or display. That is, when activated by a signal from the personal computer 150, the digitizing board will collect video and/or digital data and images from video camera 110 at that instant and store into digital data. The digital data produced is stored in memory and made available to personal computer 150 for analysis.

Figure 1B:
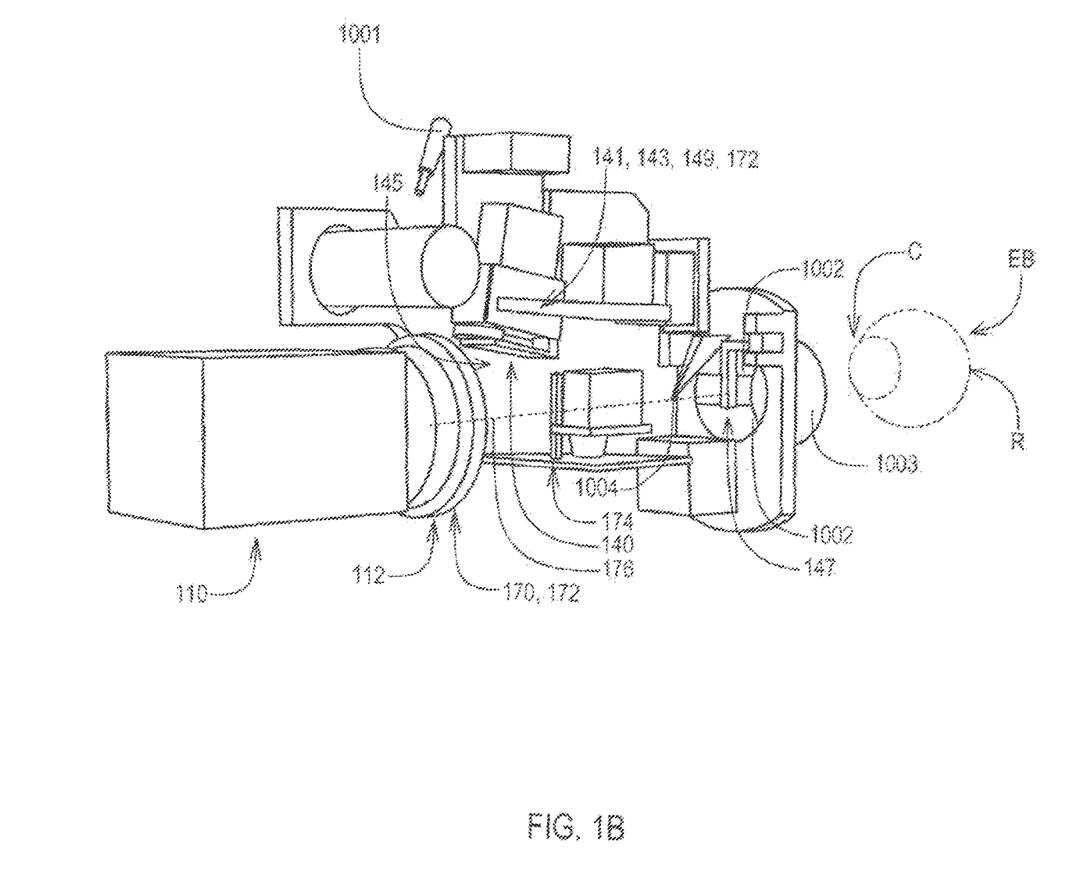
FIG. 1B illustrates a side perspective view of a camera assembly, in accordance with one embodiment of the present invention.

FIG. 1B illustrates a side perspective view of a camera housing 120 of the chinrest and joystick assembly 130, in accordance with one embodiment of the present invention. The camera housing 120 containing the video camera 110 illumination source(s) and optics 140 is proximate to a sectioned patient eyeball EB with a cornea C and a retina R. Housing 120 may be cylindrical or of any other suitable shape. The housing 120 has no forward protruding parts, which prevents accidental direct contact of any part of the apparatus for imaging an eye 100 with the patient's cornea C or facial features during movement of the housing 120 relative to the patient's eyes. This is advantageous since there is no contact with the patient's cornea C to accomplish examination and image capture. The external housing 120 and the optics have been designed to maintain some distance to the cornea C, increasing patient comfort while any testing is being performed. A flexible interface such as a rubber cup 180 can be provided at the interface between the housing 120 and the patient's eyeball EB.

The inclusion of illumination source optics 140, camera optics 112 and the video camera 110 in the camera housing 120 provides a high degree of accessibility. By placing all elements of the apparatus for imaging an eye 100 in one camera housing 120, allows for an affordable design. Additionally, the relatively small design of the apparatus for imaging an eye 100 compared to that of a fundus camera for observation and image capture provides for a shorter and more efficient optical pathway. The compact design and simplicity of optics 112,140 reduces production costs and permits greater ease of use by the operator. The design of the apparatus for imaging an eye 100 allows imaging through a smaller pupil as compared to a fundus camera.

Video camera 110 is relatively compact and incorporates a color or monochrome CCD, CMOS, or multi/hyper-spectral image sensor. The focus of the patient may also be achieved by focus of internal optical elements of the digital camera. Lens contained inside camera 100 may be focused automatically or manually by observing the image displayed on an observation video monitor. Alternatively, an electronic auto-focusing control system could be provided for automatically adjusting the focus of lens inside camera 100. The video camera 110 can also contain a monochrome or color CCD or CMOS sensor (not shown).

The observation optics 112 associated with the video camera 110 include the lens 170, an observation aperture 172, and a filter 174. The observation aperture 172 and the filter 174 transmit light reflected from the retina R to the lens 170 and to the video camera 110. The filter 174 is an infrared stepping filter (or other filter for other imaging procedures) which improves the contrast of the image seen by the video camera 110.

Indo-cyanine green angiography, color fundus photography, auto-fluorescence, or fluorescein angiography, curcumin fluorescence imaging, or other filter sets may be utilized by the apparatus for imaging an eye 100. These filters will be mounted so as to be selectively rotatable in and out of the view axis of the video camera 110 according to the function being performed. The rotation may be accomplished manually or under computer servo control.

The projection optics 140 of the invention projects light onto the retina R, off axis at an angle to the central axis 176 of lens 170 of video camera 110. The projection optics 140 includes a lamp 141, a lamp lens group 143, a mirror 145, and a projection aperture 172. A control 1001 is provided to adjust the intensity and position of the lamp 141, either manually or under the control of the computer system 150. The control is also used to sequentially control multiple lamps 141, shifting optical elements, and flipping masks 147, LED flipping internal fixation pointer 1004, and image capture trigger.

The light from lamp 141 passes through aperture 149 and the series of lamp lens group 143 that typically has two lenses. The lenses of lamp lens group 143 concentrate the light output of lamp 141. Lamp lens group 143 may consist of multiple lenses or a single aspheric lens. The light is then deflected by mirror 145 which is placed at a critical pitch angle relative to the video camera 110 and the projection optics 112. The light passes from the mirror 145 past the flipping mask 147 which concentrates the light. The light then passes through a plurality of small pupil masks 1002. The light then passes through the objective lens 1003. The light then passes past the cornea C and is projected onto retina R.

All the masks and apertures used, such as flipping mask 147 and aperture 149 and 1002, are appropriately sized apertures. Although the lamp 141 has been described as a generalized LED lamp, it should be noted that the lamp 141 can be any source of radiant energy. In one embodiment, the lamp 141 is an infrared illumination source, and the specifications of filter 174 are adjusted accordingly to pass the wavelength of the lamp 141. Infrared illumination may be particularly desirable for alignment prior to acquiring images without the problems generated by lack of pupil dilation. The image can be captured in a relatively dark room using infrared illumination, so that the eye being imaged is naturally dilated. There is also a means for sequentially turning the light source on and off in synchronization with image capture under each condition, which is a computer system 150, further described in FIG. 1C.

In another embodiment which addresses the problems caused by lack of pupil dilation during imaging, the lamp 141 may be strobed in full color, red free, NIR or other wavelength (based on imaging procedure desired) during image acquisition rather than being kept on constantly, thereby preventing the energy of lamp 141 from narrowing the pupil prior to image capture. Because of the unique design of the projection optics 140 and the capabilities of the image processing and analysis software employed, useful image data from each image can be collected with minimum pupil dilation. Specifically, the pupils of the eye being imaged may have a diameter of as little as 2 mm. The projection optics 140 projects light onto the retina R off axis from the observation path of video camera 110. Another embodiment places an adjustable mask 1002 adjacent to objective lens 1003 that adjust to the patient's pupil to optimize the image when the pupil is small.

Figure 1C:
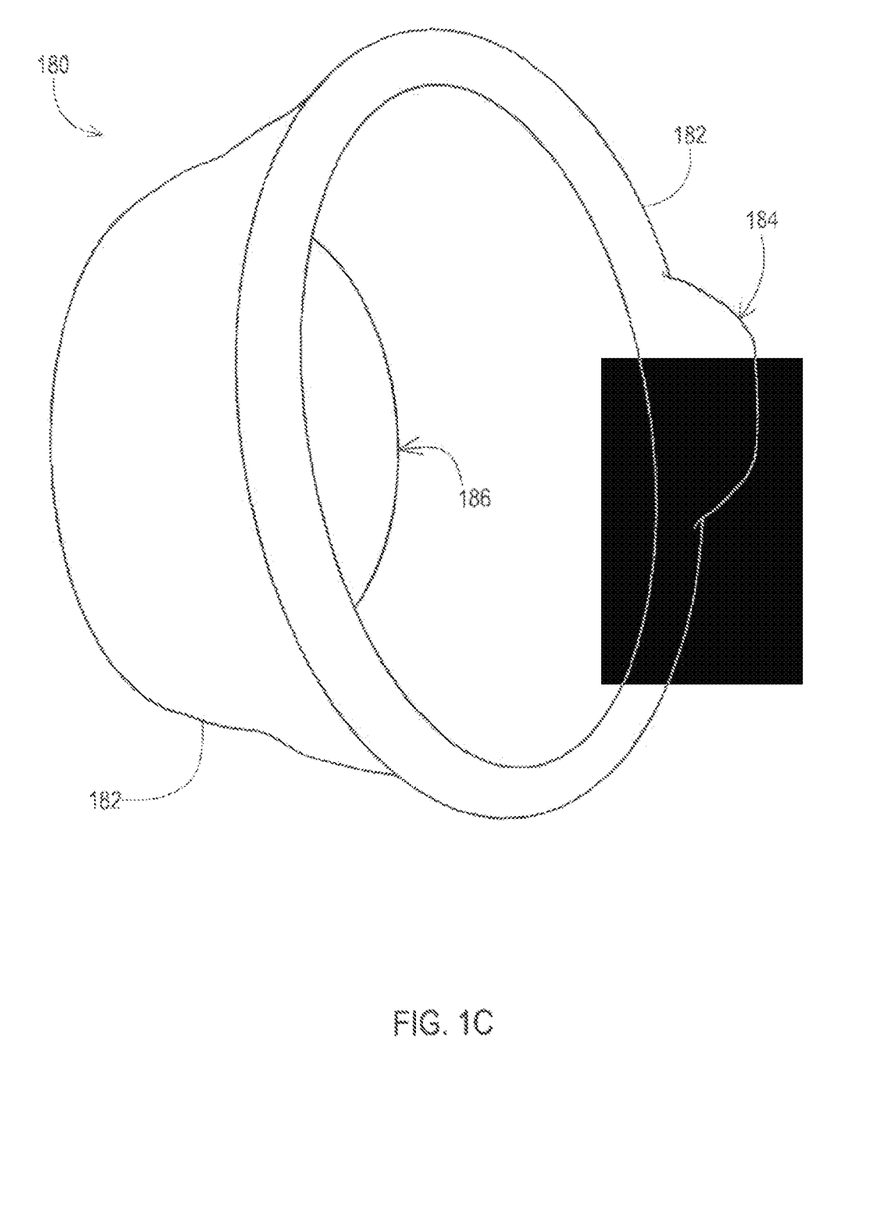
FIG. 1C illustrates a front overhead perspective view of an eyecup, in accordance with one embodiment of the present invention.

FIG. 1C illustrates a front overhead perspective view of an eyecup 180, in accordance with one embodiment of the present invention. The eyecup 180 protrudes outward from the perimeter 182 at an approximate 10% increase at the approximate 0° 184 and 180° degree 186 positions on the perimeter 182. Further details regarding the eyecup 180 are described in FIG. 3 and its description.

Figure 1D:
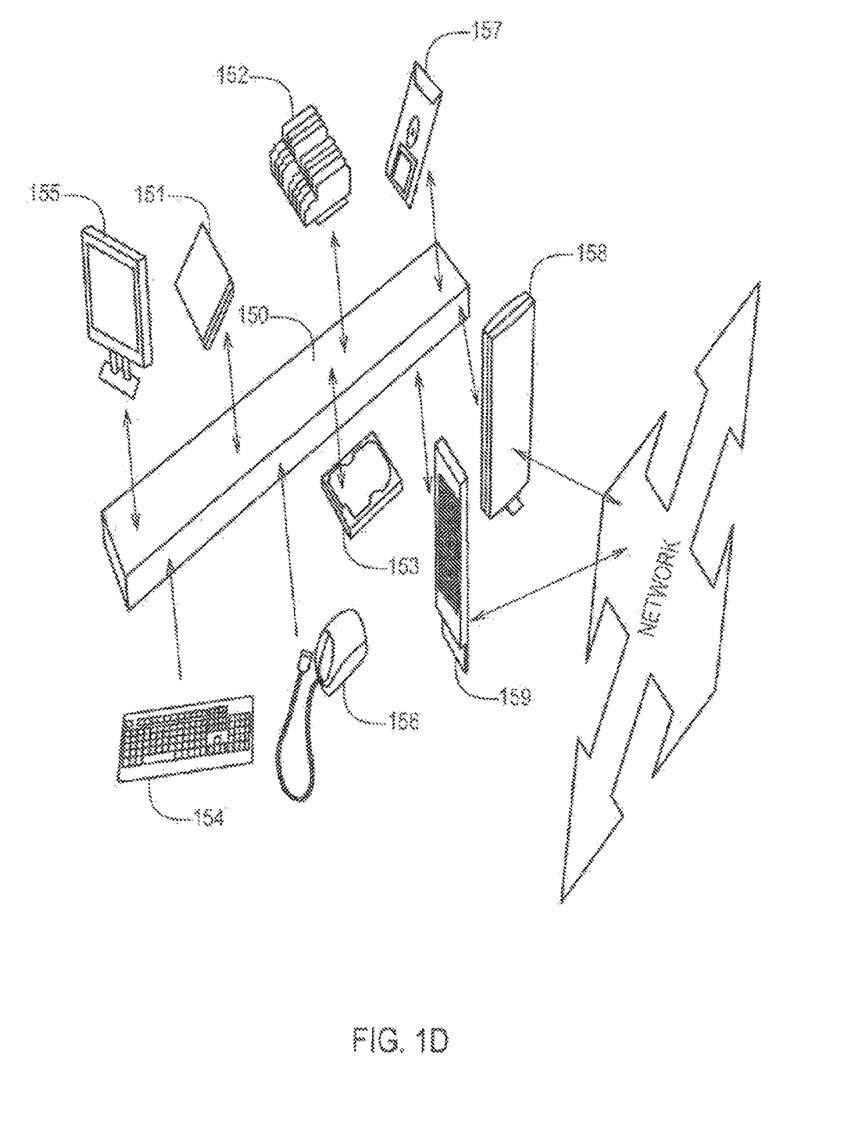
FIG. 1D is an exploded diagonal side perspective diagram of a computer system, in accordance with one embodiment of the present invention.

FIG. 1D is an exploded diagonal side perspective diagram of a computer system 150, in accordance with one embodiment of the present invention. Such a computer system 150 includes a processing unit such as a CPU 151 connected by a bus to a random access memory or RAM 152, a storage device 153, a keyboard 154, a display 155 and a mouse 156. In addition, there is software 157 for entry of data embodying the apparatus for imaging an eye 100. An example of a computer system 150 can be a Dell personal computer operating on the Microsoft Windows operating system, or Linux, Macintosh, etc. The invention can also be used on a laptop computer, cell phone, PDA, Apple™ Mac™, tablet, or other computerized device. The computerized system 150 can also be used in combination with a wireless modem 158 or network interface card 159.

The various method embodiments of the invention will be generally implemented by a computer executing a sequence of program instructions for carrying out the steps of the method, assuming all required data for processing is accessible to the computer. The sequence of program instructions may be embodied in a computer program product comprising media storing the program instructions. As will be readily apparent to those skilled in the art, the present invention can be realized in hardware, software, or a combination of hardware and software. Any kind of computer/server system(s) or other apparatus adapted for carrying out the methods described herein is suited. A typical combination of hardware and software could be a general-purpose computer system with a computer program that, when loaded and executed, carries out the method, and variations on the method as described herein.

Any combination of one or more computer usable or computer readable medium(s) may be utilized. Specific examples of the computer-readable medium can include a hard disk, a random access memory (RAM), a read-only memory (ROM), an erasable programmable read-only memory (EPROM), or flash memory or a portable compact disc read-only memory (CD-ROM). In the context of this document, a computer-usable or computer-readable medium may be any medium that can be used by or in connection with the instruction execution system or apparatus. Computer program code for carrying out operations of the overall method may be written in any combination of one or more programming languages. The program code may execute entirely on the user's computer, partly on the user's computer, as a stand-alone software package, partly on the user's computer and partly on a remote computer or entirely on the remote computer or server.

These computer program instructions may also be stored in a computer-readable medium that can direct a computer or other programmable data processing apparatus to function in a particular manner, such that the instructions stored in the computer readable medium produce an article of manufacture including instructions means which implement the function specified in the steps.

The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions specified.

Figure 2:
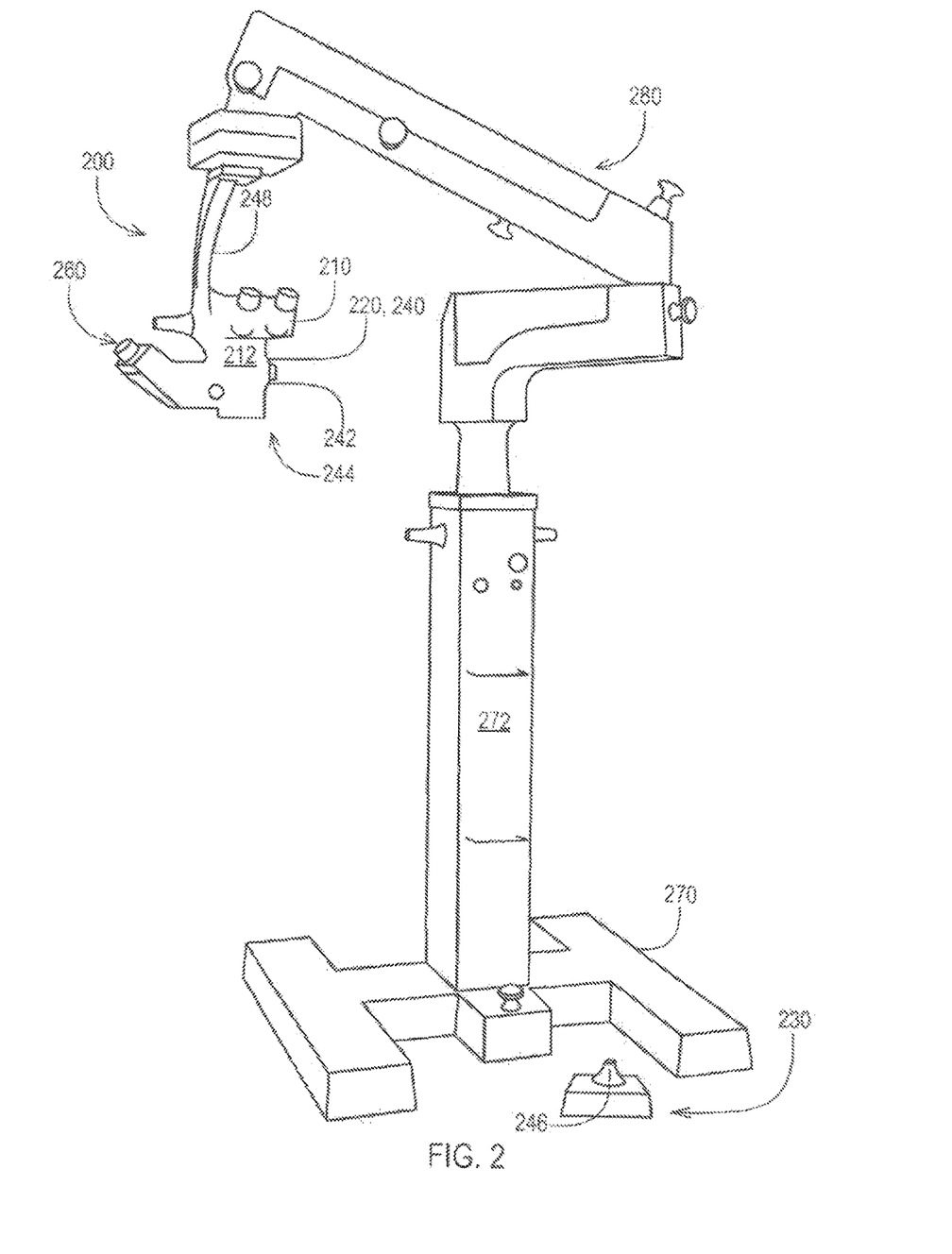
FIG. 2 illustrates a side perspective view of an apparatus for imaging an eye utilized in combination with a microscope, in accordance with one embodiment of the present invention.

FIG. 2 illustrates a side perspective view of an apparatus for imaging an eye 200 utilized in combination with a microscope 260, in accordance with one embodiment of the present invention. FIG. 2 illustrates a side perspective view of an apparatus for imaging an eye 100 that has all of the same components of the apparatus for imaging an eye 100 described in FIG. 1A, except the microscope 260 and the computer system 150. The apparatus for producing an image of an eye 200 includes a video camera 210, video camera optics 212, a camera housing 220 mounted on a patient alignment assembly 230 and illumination source optics 240. The microscope assembly 230 includes a support 242, a movable base 244, and housing support 248. The position of the camera housing 220 relative to the head support 242 can be adjusted in both gross and fine increments using the joystick 246. The microscope 260 can be any suitable microscope that can be used in combination with the apparatus for imaging an eye 200.

In one embodiment of the apparatus and method, OCT data is presented with traditional OCT display modalities and/or en face to produce a plurality of familiar retinal images.

In one embodiment of the apparatus and method, OCT is performed using a plurality of specific wavelengths that allow for the visualization of amyloid in the retina and the brain. A plurality of OCT data sets are obtained and analysis is performed to identify a plurality of spectral signature components of the amyloid. These spectral components that correspond to the amyloid are subsequently displayed in the OCT data sets that include an en face presentation. Spectral signal characteristics can be combined with other specific spectral components to render traditional OCT data sets in combination with the amyloid spectral data set.

In another embodiment of the apparatus and method, a minimum threshold technique in combination with an adaptive spectral windowing technique is applied to the data sets to render visualization of previous unseen features in the OCT data sets. In another embodiment of the apparatus and method, this technique is applied to not only amyloid but also other pathology and also anatomical features of the retina.

In another embodiment of the apparatus and method, the OCT device is operated at a plurality of different and specific spectral wavelengths to tease out desired signature and information.

In another embodiment of the apparatus and method, the apparatus and method utilizes multispectral imaging to image amyloid and other retinal pathology and features without the use of dyes or contrast agents. In another embodiment of the apparatus and method, this is accomplished via optical multispectral imaging and/or autofluorescence techniques in which the specific amyloid signal is identified and presented.

In another embodiment of the apparatus and method, curcumin (which binds to the amyloid) is used as a contrast agent in combination with OCT to discreetly identify the amyloid. In another embodiment of the apparatus and method, curcumin is used as a contrast agent in combination with multispectral optical and/or autofluorescence imaging to discreetly identify amyloid in the retina.

Another embodiment of the apparatus and method, includes a method of diagnosing macular degeneration and other eye diseases in a mammal that administers a fluorescent marker to the mammal for staining A beta peptides, imaging the mammal's retina with optical coherence tomography OCT, examining the data sets for stained A beta peptides and diagnosing the mammal as having macular degeneration or another eye disease if stained A beta peptides are present.

Another embodiment of the apparatus and method, wherein a fluorescent marker is selected from the group including but not limited to curcumin, curcumin derivatives, Thioflavin S and derivatives, Thioflavin T and derivatives, Congo Red and derivatives, methoxy-X04, Pittsburgh CompoundB (PiB), DDNP, Chrysamine-G and combinations thereof.

Another embodiment of the apparatus and method, wherein the OCT system is used with components including a spectrometer, a fluorescence microscope, a stereomicroscope, a mercury arc lamp, a variable wavelength light source, a xenon arc lamp, and LED, a tunable light source or swept source, a CCD gated camera, a color digital camera, an acoustic-optic tunable filter-based spectral image acquisition system, adaptive optics, imaging software, and combinations thereof.

Another embodiment of the apparatus and method, for the prognosing of macular degeneration and other eye disease in a mammal that includes identification of A beta peptides, imaging the subject's retina with OCT and/or multispectral imaging/autofluorescence, examining the images for A beta peptides, quantitating the increase/decrease of A beta peptides in the subject's retina, as compared to a prior diagnosis and rendering a prognosis based upon the level of A beta peptides in the subject's retina including but not limited to number, area and volume.

Another embodiment of the apparatus and method, for the prognosing of macular degeneration and other eye disease in a mammal that includes identification of A beta peptides, imaging the subject's retina with OCT and/or multispectral imaging/autofluorescence, examining the images for A beta Peptides, quantitating the increase/decrease of A beta peptides in the subject's retina, as compared to a prior diagnosis in combination with a normative database and rendering a prognosis based upon the level of A beta peptides in the subject's retina (including but not limited to number, area and volume).

Another embodiment of the apparatus and method, for the prognosing of traumatic brain injury and other neurodegenerative disease in a mammal that includes identification of A beta peptides, imaging the subject's retina with OCT and/or multispectral imaging/autofluorescence, examining the images for A beta Peptides, quantitating the increase/decrease of A beta peptides in the subject's retina, as compared to a prior diagnosis in combination with a normative database and rendering a prognosis based upon the level of A beta peptides in the subject's retina (including but not limited to number, area and volume).

Another embodiment of the apparatus and method, is to perform a Maximum/Minimum Intensity Projection (MIP/MiniP) and/or in combination with other specific discreet spectral signatures on OCT and/or multispectral images for the identification of amyloid in the retina (or brain) and other retinal features and pathology including but not limited to choroidal neovascularization. Maximum intensity projection (MIP) and minimum intensity projection (MiniP) are defined as volume rendering techniques in which suitable editing methods are used to define a volume of interest (VOI). All of the image data set may be used, or the volume may be confined to a region of interest (ROI).

In one embodiment of the apparatus and method, only desired features are included or excluded from the VOI and actual images are generated by projecting the volume of interest into a viewing plane and displaying the maximum OCT scan numbers (for MIP) or the minimum OCT numbers (for MiniP) that are encountered along the direction of the projection to ensure that optimum contrast is produced between small, high-contrast structures and surrounding tissues.

Figure 3:
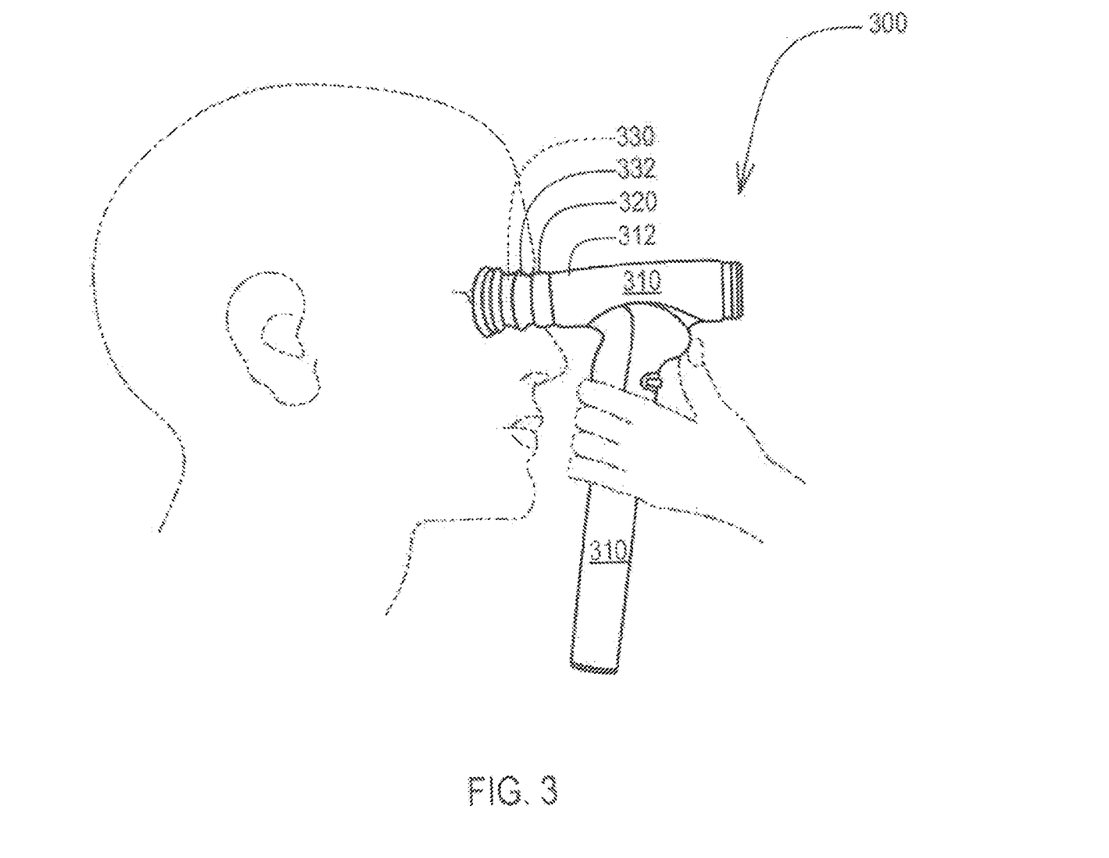
FIG. 3 illustrates a side perspective view of an apparatus for imaging an eye that is hand-held, in accordance with one embodiment of the present invention.

FIG. 3 illustrates a side perspective view of a hand held apparatus for imaging an eye 300, in accordance with one embodiment of the present invention. The hand held apparatus for imaging an eye 300 includes all of the same components of the apparatus for imaging an eye 100 described in FIG. 1B and can be used in combination with a microscope 260 (FIG. 2) or a computer system 150 (FIG. 1A). The hand held apparatus for imaging an eye 300 utilizes a hand-held housing 310 instead of a camera housing 120 as described in FIGS. 1A and 1B, but utilizes all of the same optical and electrical components disposed within the hand-held housing 310.

The hand-held apparatus for producing an image of an eye 300 may also utilize a flexible eyecup 320 that could be fixed to the hand-held apparatus for producing an image of an eye 300, or be utilized as a disposable flexible eyecup that attaches to the end 312 of the apparatus for producing an image of an eye for use on each patient. The flexible eyecup 320 could be made of baffled flexible material 322 such as rubber, plastic, or any type of suitable material that gently surrounds the patient's eye to create a darkened environment and could also be used to hold a patient's eyelids open. The flexible eyecup 320 could have an angular spring internal mechanism 330 that holds the patient's eyelids open. The baffles 322 are flexible to allow for adjustable and proper positioning around the patient's eye.

Figure 4:
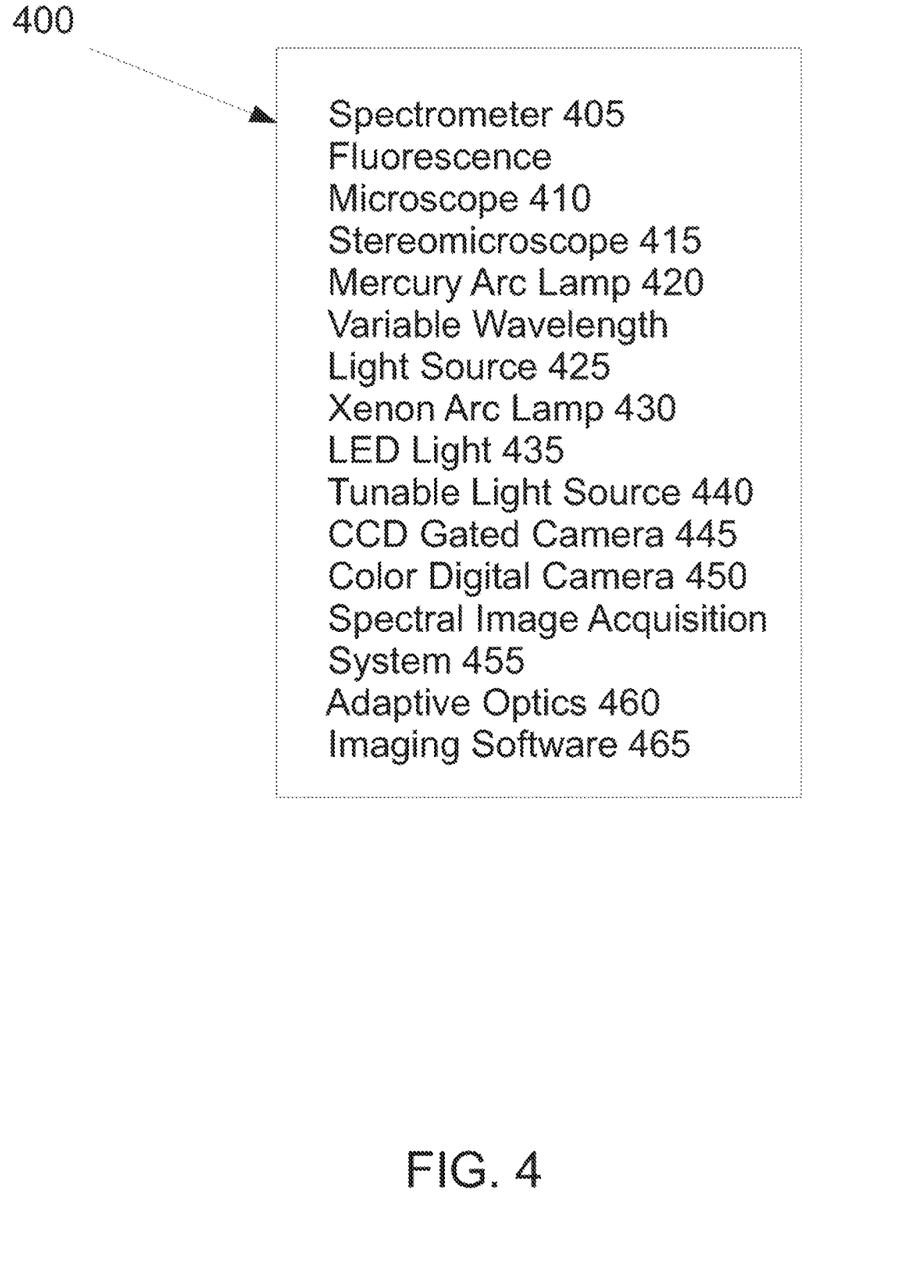
FIG. 4 is a block diagram of various components that can be utilized in combination with an apparatus for imaging an eye, in accordance with one embodiment of the present invention.

FIG. 4 is a block diagram of a plurality of various components 400 that can be utilized in combination with an apparatus for imaging an eye, in accordance with one embodiment of the present invention.

These components 400 include are selected from the group consisting of a spectrometer 405, a fluorescence microscope 410, a stereomicroscope 415, a mercury arc lamp 420, a variable wavelength light source 425, a xenon arc lamp 430, an LED light 435, a tunable light source or swept source 440, a CCD gated camera 445, a color digital camera 450, an acoustic-optic tunable filter-based spectral image acquisition system 455, a plurality of adaptive optics 460, imaging software 465 and any combinations thereof. The apparatus 100 is utilized in combination with one or more contrasting agents that are selected from the group consisting of curcumin, curcumin derivatives, Thioflavin S and derivatives, Thioflavin T and derivatives, Congo Red and derivatives, methoxy-X04, Pittsburgh CompoundB (PiB), DDNP, Chrysamine-G and any combination thereof.

Figure 5:
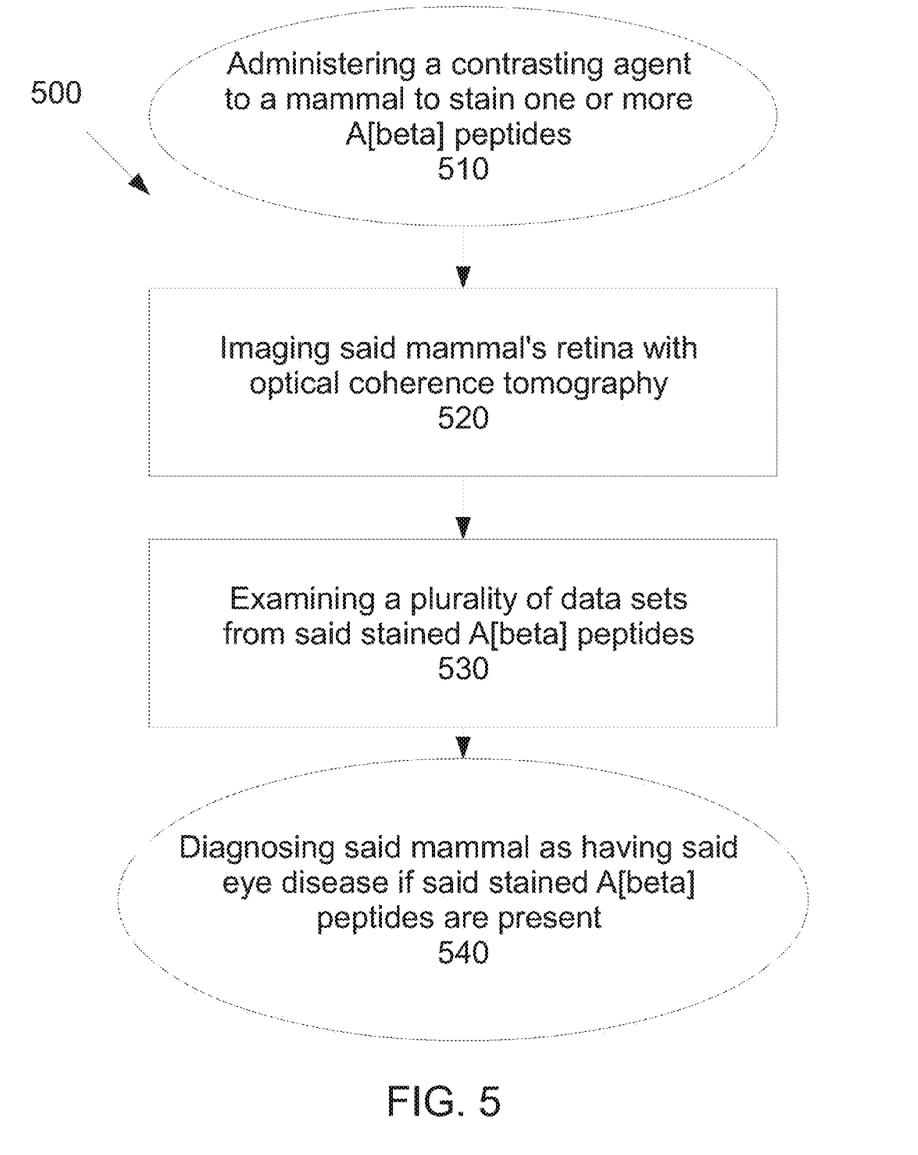
FIG. 5 is a method for diagnosing an eye disease in a mammal, in accordance with one embodiment of the present invention.

FIG. 5 is a method 500 for diagnosing an eye disease in a mammal, in accordance with one embodiment of the present invention.

The steps of the method 500 include administering a contrasting agent to the mammal to stain one or more A beta peptides 510, imaging the mammal's retina with optical coherence tomography 520, examining a plurality of data sets from the stained A beta peptides 530 and diagnosing the mammal as having the eye disease if the stained A beta peptides are present 540. The administering a contrasting agent to the mammal to stain one or more A beta peptides 510 can be accomplished with one or more contrasting agents are selected from the group consisting of curcumin, curcumin derivatives, Thioflavin S and derivatives, Thioflavin T and derivatives, Congo Red and derivatives, methoxy-X04, Pittsburgh CompoundB (PiB), DDNP, Chrysamine-G and any combination thereof. The imaging the mammal's retina with optical coherence tomography 520 can be accomplished with the apparatus to produce an image of an eye of a patient that is previously described in FIGS. 1A and 1B and its components that include a digital video camera that includes video camera optics, illumination source optics and a camera housing with a perimeter that houses the video camera optics and the illumination source optics, a slit lamp chinrest and joystick assembly that includes an adjustable head support, a movable base, a joystick that adjusts a position of the camera housing relative to the head support and the housing support that mounts the video camera, a rubber eyecup that provides an interface between the camera housing and the patient's eye that protrudes outward from the perimeter and a computer system. The examining a plurality of data sets from the stained A beta peptides 530 is accomplished typically with the computer system previously described in FIG. 1D. The diagnosing the mammal as having the eye disease if the stained A beta peptides are present 540 is straightforwardly an indication characteristic of the stained A beta peptides.

Figure 6:
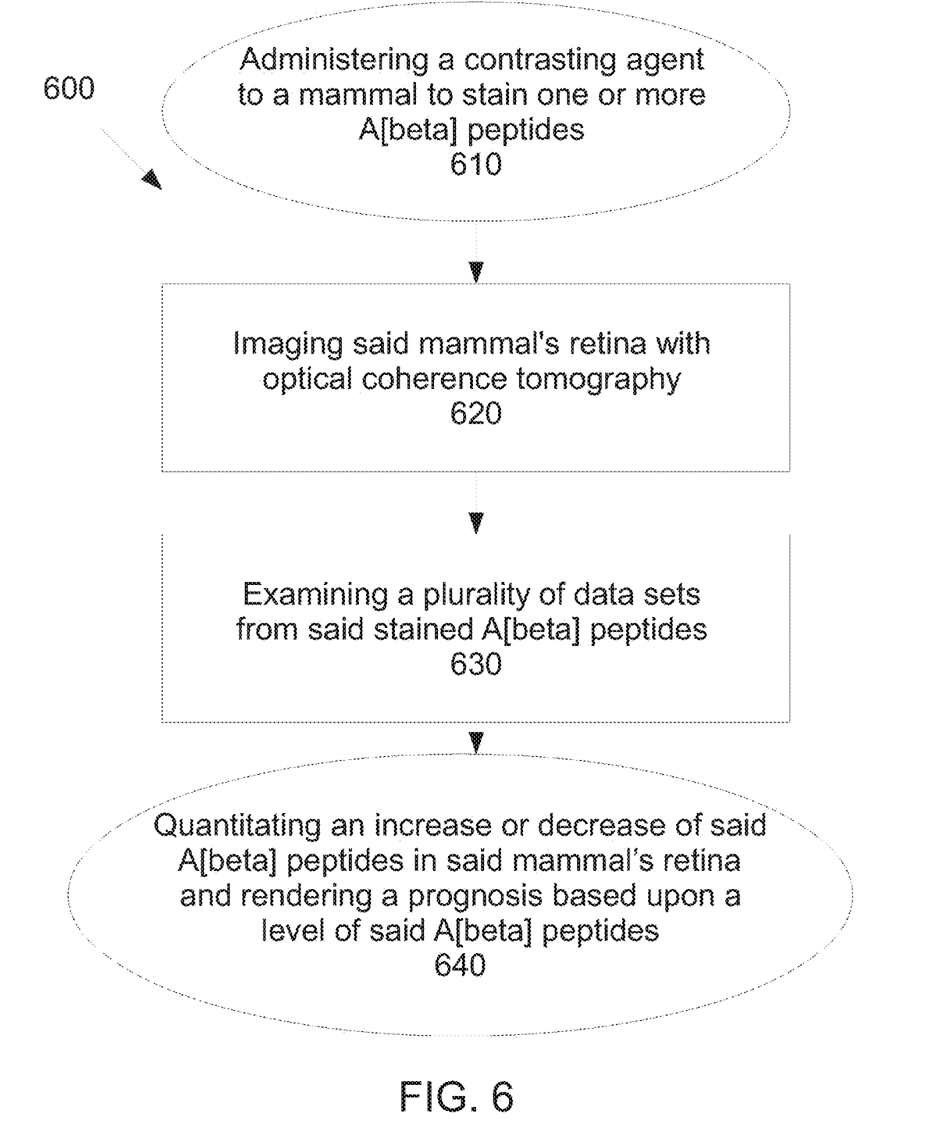
FIG. 6 is a method for diagnosing an eye disease in a mammal, in accordance with one embodiment of the present invention.

FIG. 6 is a method 600 for diagnosing an eye disease in a mammal, in accordance with one embodiment of the present invention.

The method 600 includes administering a fluorescent marker to the mammal to stain one or more A beta peptides 610, imaging the mammal's retina with optical coherence tomography 620, examining a plurality of data sets from the stained A beta peptides 630 and quantitating an increase or decrease of the A beta peptides in the mammal's retina and rendering a prognosis based upon a level of the A beta peptides 640.

The administering a contrasting agent to the mammal to stain one or more A beta peptides 610 can be accomplished with one or more contrasting agents are selected from the group consisting of curcumin, curcumin derivatives, Thioflavin S and derivatives, Thioflavin T and derivatives, Congo Red and derivatives, methoxy-X04, Pittsburgh CompoundB (PiB), DDNP, Chrysamine-G and any combination thereof. The imaging the mammal's retina with optical coherence tomography 620 can be accomplished with the apparatus to produce an image of an eye of a patient that is previously described in FIGS. 1A and 1B and its components that include a digital video camera that includes video camera optics, illumination source optics and a camera housing with a perimeter that houses said video camera optics and said illumination source optics, a slit lamp chinrest and joystick assembly that includes an adjustable head support, a movable base, a joystick that adjusts a position of said camera housing relative to said head support and the housing support that mounts the video camera, a rubber eyecup that provides an interface between the camera housing and the patient's eye that protrudes outward from the perimeter and a computer system. The examining a plurality of data sets from the stained A beta peptides 630 is accomplished typically with the computer system previously described in FIG. 1D. The quantitating an increase or decrease of the A beta peptides in the mammal's retina and rendering a prognosis based upon a level of the A beta peptides 640 is accomplished typically with the computer system previously described in FIG. 1D.

Figure 7:
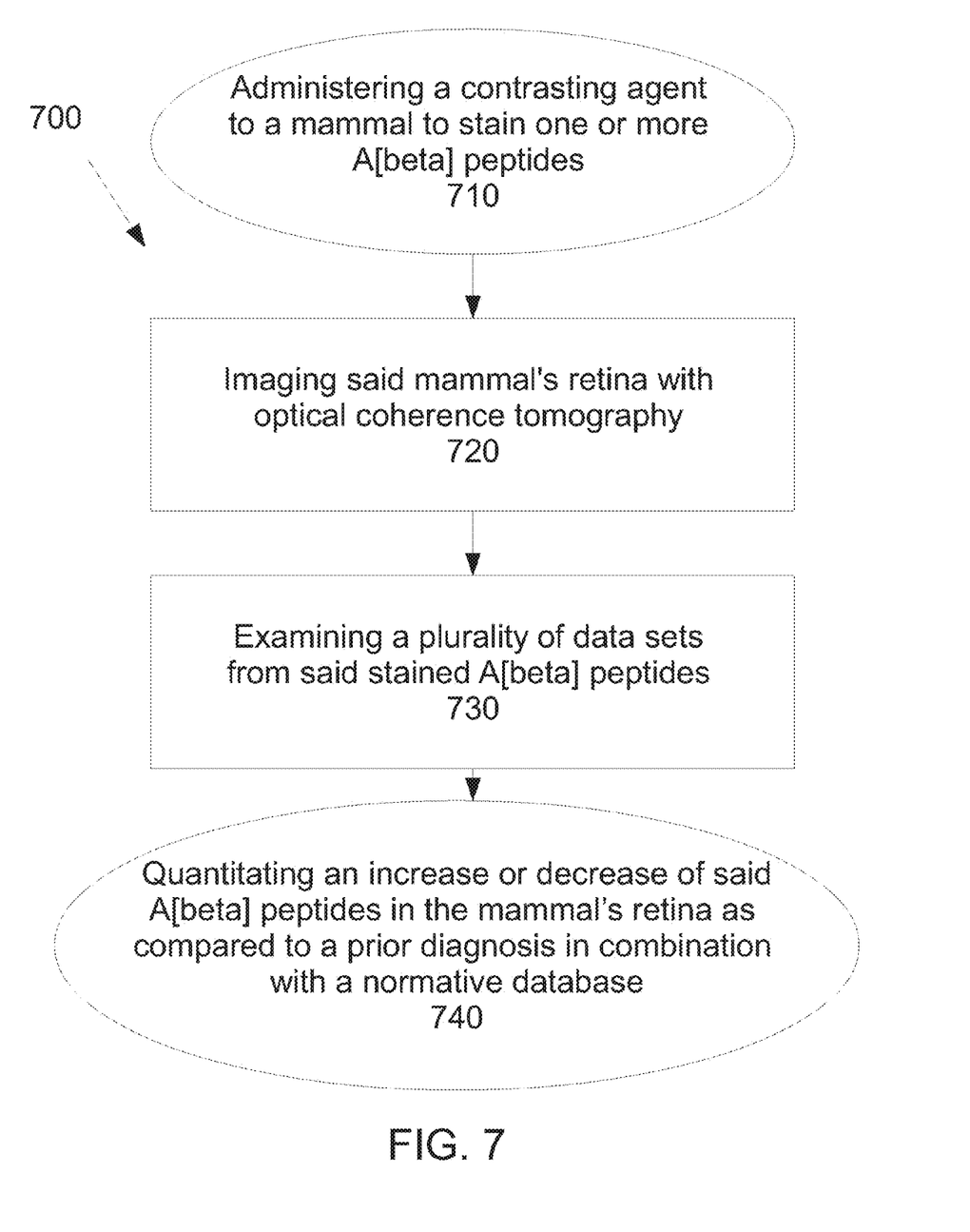
FIG. 7 is a method for diagnosing an eye disease in a mammal, in accordance with one embodiment of the present invention.

FIG. 7 is a method 700 for diagnosing an eye disease in a mammal, in accordance with one embodiment of the present invention.

The method 700 includes administering a fluorescent marker to the mammal to stain one or more A beta peptides 710, imaging the mammal's retina with optical coherence tomography 720, examining a plurality of data sets from the stained A beta peptides 730 and quantitating an increase or decrease of the A beta peptides in the mammal's retina as compared to a prior diagnosis in combination with a normative database and rendering a prognosis based upon a level of the A beta peptides 740.

The administering a contrasting agent to the mammal to stain one or more A beta peptides 710 can be accomplished with one or more contrasting agents are selected from the group consisting of curcumin, curcumin derivatives, Thioflavin S and derivatives, Thioflavin T and derivatives, Congo Red and derivatives, methoxy-X04, Pittsburgh CompoundB (PiB), DDNP, Chrysamine-G and any combination thereof. The imaging the mammal's retina with optical coherence tomography 720 can be accomplished with the apparatus to produce an image of an eye of a patient that is previously described in FIGS. 1A and 1B and its components that include a digital video camera that includes video camera optics, illumination source optics and a camera housing with a perimeter that houses said video camera optics and said illumination source optics, a slit lamp chinrest and joystick assembly that includes an adjustable head support, a movable base, a joystick that adjusts a position of said camera housing relative to said head support and the housing support that mounts the video camera, a rubber eyecup that provides an interface between the camera housing and the patient's eye that protrudes outward from the perimeter and a computer system. The examining a plurality of data sets from the stained A beta peptides 730 is accomplished typically with the computer system previously described in FIG. 1D. The quantitating an increase or decrease of the A beta peptides in the mammal's retina as compared to a prior diagnosis in combination with a normative database and rendering a prognosis based upon a level of the A beta peptides 740.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A method for diagnosing an eye disease, comprising the steps of:
    administering a contrasting agent to the retina of a mammal to stain at least one A beta peptide;
    imaging the mammal's retina with optical coherence tomography to obtain a plurality of data sets;
    examining the spectra of the plurality of data sets from the stained A beta peptide; and
    diagnosing the mammal as having the eye disease if the spectra obtained correspond to reference signature spectra amyloid characteristic of the eye disease.

2. The method according to claim 1, wherein the administering a contrasting agent to the mammal to stain at least one A beta peptide is accomplished with at least one contrasting agent selected from the group consisting of curcumin, curcumin derivatives, Thioflavin Sand derivatives, Thioflavin T and derivatives, Congo Red and derivatives, methoxy-X04, Pittsburgh CompoundB, DDNP, and Chrysamine-G.

3. The method according to claim 1, wherein the imaging the mammal's retina with optical coherence tomography is accomplished with the apparatus to produce an image of an eye of the mammal that includes a digital video camera that includes video camera optics, illumination source optics and a camera housing with a perimeter that houses the video camera optics and the illumination source optics, a slit lamp chinrest and joystick assembly that includes an adjustable head support, a movable base, a joystick that adjusts a position of the camera housing relative to the head support and the housing support that mounts the video camera, a rubber eyecup that provides an interface between the camera housing and the mammal's eye that protrudes outward from the perimeter and a computer system.

4. The method according to claim 1, wherein the examining the spectra of the plurality of data sets from the stained A beta peptides is accomplished with a computer system.

5. The method according to claim 1, wherein the diagnosing the mammal as having the eye disease if the stained A beta peptides are present is an indication characteristic of the stained A beta peptides.

6. A method for diagnosing an eye disease, comprising the steps of:
    administering a fluorescent marker to the mammal to stain at least one A beta peptide;
    imaging the mammal's retina with optical coherence tomography to obtain a plurality of data sets;
    examining the plurality of data sets from the stained A beta peptides; and
    quantitating an increase or decrease of the A beta peptides in the mammal's retina and rendering a diagnosis of eye disease based upon the quantification of the increase or decrease in the A beta peptides.

7. The method according to claim 6, wherein the administering a contrasting agent to the mammal to stain at least one A beta peptide is accomplished with at least one contrasting agent selected from the group consisting of curcumin, curcumin derivatives, Thioflavin Sand derivatives, Thioflavin T and derivatives, Congo Red and derivatives, methoxy-X04, Pittsburgh CompoundB, DDNP, and Chrysamine-G.

8. The method according to claim 6, wherein the imaging the mammal's retina with optical coherence tomography includes using a digital video camera that includes video camera optics, illumination source optics and a camera housing with a perimeter that houses the video camera optics and the illumination source optics, a slit lamp chinrest and joystick assembly that includes an adjustable head support, a movable base, a joystick that adjusts a position of the camera housing relative to the head support and the housing support that mounts the video camera, a rubber eyecup that provides an interface between the camera housing and the patient's eye that protrudes outward from the perimeter and a computer system.

9. The method according to claim 6, wherein the examining the plurality of data sets from the stained A beta peptides is accomplished with a computer system.

10. The method according to claim 6, wherein the diagnosing the mammal as having the eye disease if the stained A beta peptides are present is an indication characteristic of the stained A beta peptides.

11. A method for diagnosing an eye disease, comprising the steps of:
    administering a fluorescent marker to the mammal to stain one or more A beta peptides;
    imaging the mammal's retina with optical coherence tomography to obtain a plurality of data sets;
    examining the plurality of data sets from the stained A beta peptides; and
    quantitating an increase or decrease of the A beta peptides in the mammal's retina as compared to a prior diagnosis in combination with a normative database, and rendering a diagnosis of eye disease based upon the qualification of the increase or decrease of the A beta peptides.

12. The method according to claim 11, wherein the administering a contrasting agent to the mammal to stain at least one A beta peptide is accomplished with at least one contrasting agent selected from the group consisting of curcumin, curcumin derivatives, Thioflavin Sand derivatives, Thioflavin T and derivatives, Congo Red and derivatives, methoxy-X04, Pittsburgh CompoundB, DDNP, and Chrysamine-G.

13. The method according to claim 11, wherein the imaging the mammal's retina with optical coherence tomography includes using a digital video camera that includes video camera optics, illumination source optics and a camera housing with a perimeter that houses the video camera optics and the illumination source optics, a slit lamp chinrest and joystick assembly that includes an adjustable head support, a movable base, a joystick that adjusts a position of the camera housing relative to the head support and the housing support that mounts the video camera, a rubber eyecup that provides an interface between the camera housing and the patient's eye that protrudes outward from the perimeter and a computer system.

14. The method according to claim 11, wherein the examining the plurality of data sets from the stained A beta peptides is accomplished with a computer system.

15. A computer readable storage medium containing program code for executing a program to examine the spectra of a plurality of data sets from imaging a mammal's retina with optical coherence tomography, and diagnosing whether the mammal has an eye disease by comparing the spectra to reference signature spectra characteristic of the eye disease.

* * * * *